(12) United States Patent
Heller et al.

(10) Patent No.: US 11,553,892 B2
(45) Date of Patent: Jan. 17, 2023

(54) AUTOMATED ULTRASONIC MEASUREMENT OF NUCHAL FOLD TRANSLUCENCY

(71) Applicant: KONINKLIJKE PHILIPS N.V., Eindhoven (NL)

(72) Inventors: Susan Gay Heller, Bothell, WA (US); Yayun Wan, Bothell, WA (US); Ji Cao, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 871 days.

(21) Appl. No.: 16/078,806

(22) PCT Filed: Mar. 1, 2017

(86) PCT No.: PCT/EP2017/054799
§ 371 (c)(1),
(2) Date: Aug. 22, 2018

(87) PCT Pub. No.: WO2017/149027
PCT Pub. Date: Sep. 8, 2017

(65) Prior Publication Data
US 2019/0015069 A1    Jan. 17, 2019

Related U.S. Application Data
(60) Provisional application No. 62/301,810, filed on Mar. 1, 2016.

(51) Int. Cl.
*A61B 8/08*  (2006.01)
*A61B 8/00*  (2006.01)
*A61B 8/14*  (2006.01)

(52) U.S. Cl.
CPC .......... *A61B 8/0866* (2013.01); *A61B 8/0858* (2013.01); *A61B 8/145* (2013.01);
(Continued)

(58) Field of Classification Search
CPC ....... A61B 8/0866; A61B 8/145; A61B 8/463; A61B 8/5207; A61B 8/5246;
(Continued)

(56) References Cited

U.S. PATENT DOCUMENTS 5,474,073 A   12/1995  Schwartz et al.
5,485,842 A   1/1996   Quistgaard
(Continued)

FOREIGN PATENT DOCUMENTS

EP    1685799 A1   8/2006
GB    2407636 A    5/2005
(Continued)

OTHER PUBLICATIONS

Chung, Jin-Hoon, Jae-Hyug Yang, Mi-Jin Song, Jeong-Yeon Cho, Young-Ho Lee, So-Yeon Park, Myoung-Jin Moon et al. "The distribution of fetal nuchal translucency thickness in normal Korean fetuses.", 2004, Journal of Korean Medical Science 19, No. 1, 32-36. (Year: 2004).*

(Continued)

*Primary Examiner* — Christopher Koharski
*Assistant Examiner* — Renee C Langhals

(57) ABSTRACT

An ultrasonic diagnostic imaging system is used to acquire a fetal image in a sagittal view for the performance of a nuchal translucency measurement. After a fetal image has been acquired, a zoom box is positioned over the image, encompassing a region of interest. The size of the zoom box is automatically set for the user in correspondence with gestational age or crown rump length. The system automatically tracks the region of interest within the zoom box in the presence of fetal motion in an effort to maintain the region of interest within the zoom box despite movement by the fetus.

17 Claims, 6 Drawing Sheets

(52) U.S. Cl.
CPC .............. *A61B 8/463* (2013.01); *A61B 8/469* (2013.01); *A61B 8/523* (2013.01); *A61B 8/5207* (2013.01); *A61B 8/5223* (2013.01); *A61B 8/5246* (2013.01); *A61B 8/5292* (2013.01); *A61B 8/4427* (2013.01); *A61B 8/483* (2013.01); *A61B 8/5238* (2013.01); *A61B 8/5276* (2013.01)

(58) Field of Classification Search
CPC ..... A61B 8/5292; A61B 8/0858; A61B 8/469; A61B 8/5223; A61B 8/523; A61B 8/5276; A61B 8/5238; A61B 8/483; A61B 8/4427; G16H 50/30
USPC ......................................................... 600/449
See application file for complete search history.

(56) References Cited

U.S. PATENT DOCUMENTS

| | | | |
|---|---|---|---|
| 5,720,291 | A | 2/1998 | Schwartz |
| 6,013,032 | A | 1/2000 | Savord |
| 6,050,942 | A | 4/2000 | Rust et al. |
| 6,186,950 | B1 | 2/2001 | Averkiou et al. |
| 6,375,617 | B1 | 4/2002 | Fraser |
| 6,692,438 | B2 | 2/2004 | Skyba et al. |
| 9,119,591 | B2 | 9/2015 | Lee |
| 2003/0105401 | A1* | 6/2003 | Jago ............ A61B 8/467 600/443 |
| 2005/0075567 | A1 | 4/2005 | Skyba et al. |
| 2005/0124878 | A1* | 6/2005 | Sharony ............ A61B 8/0866 600/437 |
| 2005/0240104 | A1 | 10/2005 | Shim et al. |
| 2006/0184031 | A1* | 8/2006 | Ichioka ............ A61B 8/4483 600/447 |
| 2008/0240532 | A1* | 10/2008 | Carneiro ............ G06K 9/46 382/131 |
| 2010/0063391 | A1 | 3/2010 | Kanai et al. |
| 2012/0087564 | A1* | 4/2012 | Tsujita ............ G16H 50/30 382/131 |
| 2012/0296212 | A1* | 11/2012 | Hamada ............ A61B 8/0866 600/443 |
| 2012/0310094 | A1 | 12/2012 | Miyachi |
| 2013/0245477 | A1 | 9/2013 | Imamura et al. |
| 2014/0296694 | A1 | 10/2014 | Jaworski |
| 2015/0032001 | A1 | 1/2015 | Nakata et al. |
| 2015/0148657 | A1 | 5/2015 | Shashar et al. |
| 2015/0193908 | A1 | 7/2015 | Shim et al. |
| 2015/0254839 | A1 | 9/2015 | Yoo |
| 2016/0042525 | A1 | 2/2016 | Lee et al. |

FOREIGN PATENT DOCUMENTS

| | | |
|---|---|---|
| KR | 20080004775 A | 1/2008 |
| KR | 20080004775 A | 10/2008 |
| WO | 2005054898 A1 | 6/2005 |
| WO | 2013146016 A1 | 10/2013 |

OTHER PUBLICATIONS

Karki et al "Nuchal Translucency in Normal Fetus and Its Variation With Increasing Crown Rump Length.." Kathmandu University Medical Journal , vol. 11, No. 4,Issue 44, Oct.-Dec. 2013 p. 282-286.

Jou et al "Relationship Between Fetal Nuchal Translucency and Crown-Rump Length in an Asian Population" Ultrsound Obstet Gynecol. 2001, 17, p. 111-114, Sep. 21, 1999.

K. W. Lai and E. Supriyanto, "Detection of Fetal Abnormalities Based on Three Dimensional Nuchal Translucency" Springer Briefs in Applied Sciences and Technology 2013"Medicine and Engineering related research on the Utility of two Dimensional Nuchal translucency".

Lee et al "Robust border enhancement and detection for measurement of fetal nuchal translucency in ultrasound images" Med. Bio. Eng. Comput (2007) 45: p. 1143-1152, Jul. 27, 2007.

Zoppi et al "Fetal Nuchal Translucency Screening In 12 495 Pregnancies in Sardinia" Ultrasound in Obstetrics and Gynocology, vol. 18, No. 6 Dec. 1, 2001 p. 649-651.

* cited by examiner

AUTOMATED ULTRASONIC MEASUREMENT OF NUCHAL FOLD TRANSLUCENCY

This application is the U.S. National Phase application under 35 U.S.C. § 371 of International Application No. PCT/EP2017/054799 filed on Mar. 1, 2017, which claims the benefit of Provisional Application Ser. No. 62/301,810, filed Mar. 1, 2016. These applications are hereby incorporated by reference herein.

This invention relates to medical diagnostic ultrasound systems and, in particular, to ultrasound systems and methods for performing measurements of the fetal nuchal fold and translucency.

Prenatal screening methods are routinely employed to assess the likelihood of fetal abnormalities, commonly referred to as birth defects. For example, Down syndrome or trisomy 21 is the most common cause of severe learning disabilities and accounts for approximately one-half of all chromosomal anomalies in new births. Down syndrome, the most frequent fetal chromosomal abnormality, affects approximately 1 in 800 infants. This birth defect is associated with mental retardation, structural defects involving the heart and/or the digestive tract, increased incidence of respiratory infection, high incidence of fluctuating hearing loss, and thyroid and cervical spine abnormalities. Current methods to screen prenatally for trisomy 21 involve maternal serum testing for biochemical markers and/or ultrasound evaluation of biophysical markers.

Generally, the most reliable diagnoses of Down syndrome are invasive procedures such as amniocentesis, which involves sampling the amniotic fluid, and chorionic villus sampling (CVS), which involves sampling the chorionic villi from the placenta. These invasive procedures, however, involve risk to the mother and the fetus and therefore are not routinely performed during all pregnancies. Instead, one or more noninvasive screening methods may be utilized to determine whether the likelihood of Down syndrome warrants the risk of undergoing an invasive diagnostic procedure. If the noninvasive diagnosis indicates the likelihood of an abnormality, the clinician usually moves to the next step of ordering an invasive procedure.

One noninvasive diagnostic test is the nuchal translucency measurement performed by ultrasonic imaging, which does not expose the mother or fetus to hazardous radiation. Fluid between the fetal spine and the fetal skin at the level of the fetal neck is a normal phenomenon seen in early fetal development. This fluid is in a confined and well-circumscribed space called the nuchal fold. It is well documented that an excess of fluid in this space is associated with a significant risk of trisomy 21. The nuchal skin fold is increased in cases where skin edema is present. This condition occurs in Turner's syndrome, Down's syndrome and a number of chromosomal abnormalities.

Between weeks 10 to 13 of the pregnancy, the spacing of the normal nuchal fold is less than 3 mm and after 16 weeks it should not exceed 6-7 mm. Measurements of the fetal nuchal translucency between weeks 11 and 14 are regularly used as a screening test in assessing the risk of trisomy 21. In the current ultrasound procedure the fluid amount is estimated by an anterior-posterior diameter measurement of the nuchal fold at the level of the fetal neck, with the spine of the fetus in a horizontal orientation in the ultrasound image and the image plane in a sagittal orientation through the fetal neck. Furthermore, the fetus should be floating away from the uterine wall, only the head and upper thorax should be in the measurement area, and the degree of image magnification should have the fetus occupying most of the image. Attaining all of these objectives for a good measurement is a tedious process since the image has to be captured with the fetus in a perfectly sagittal position, a challenge made difficult because the fetus is frequently moving. The fetus must also be in a neutral position when the measurement is made. Fetal body flexion will decrease the nuchal fold diameter and extension will increase it. Moreover, it is often necessary to repeatedly adjust the size and position of the zoom box over the fetus in the image, inside of which the measurement is made. Accordingly it is desirable to ease the constraints and difficulty of this diagnostic procedure through automated image analysis tools which aid the clinician in making the measurement of nuchal translucency.

In accordance with the principles of the present invention, a diagnostic ultrasound system and method are described which aids a clinician by automating measurements of nuchal translucency. In an implementation of the present invention zoom box sizing is automatically selected for the clinician and the locus of the fetus in the zoom box is tracked in real time to continually position the nuchal fold region within the zoom box.

Figure 7:
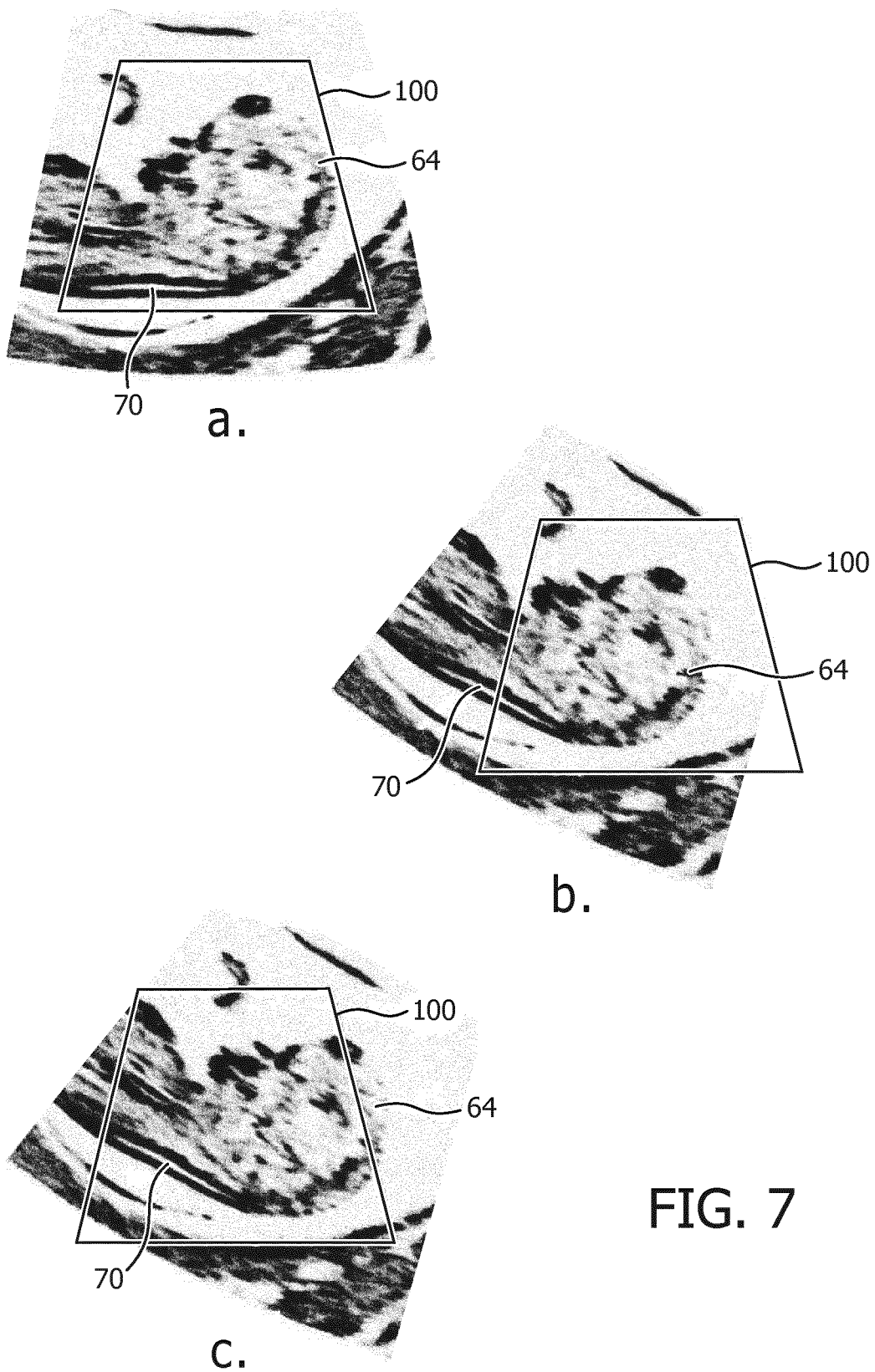

FIG. 7 *a*, *b*, and *c* illustrate zoom box tracking of the position of a fetus in accordance with the principles of the present invention.

Figure 8:
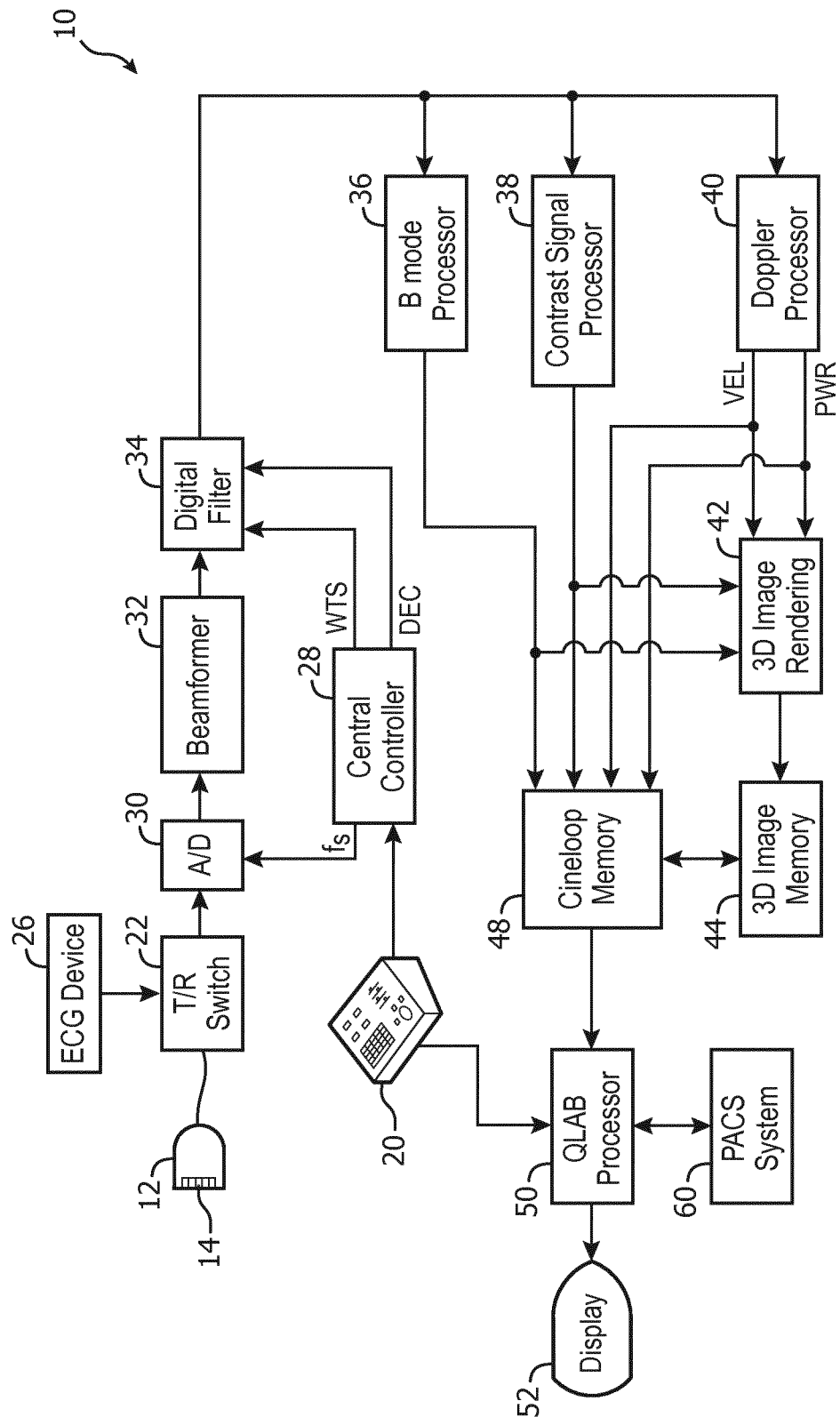

FIG. 8 illustrates in block diagram form an ultrasonic diagnostic imaging system constructed in accordance with the principles of the present invention.

Figure 1:
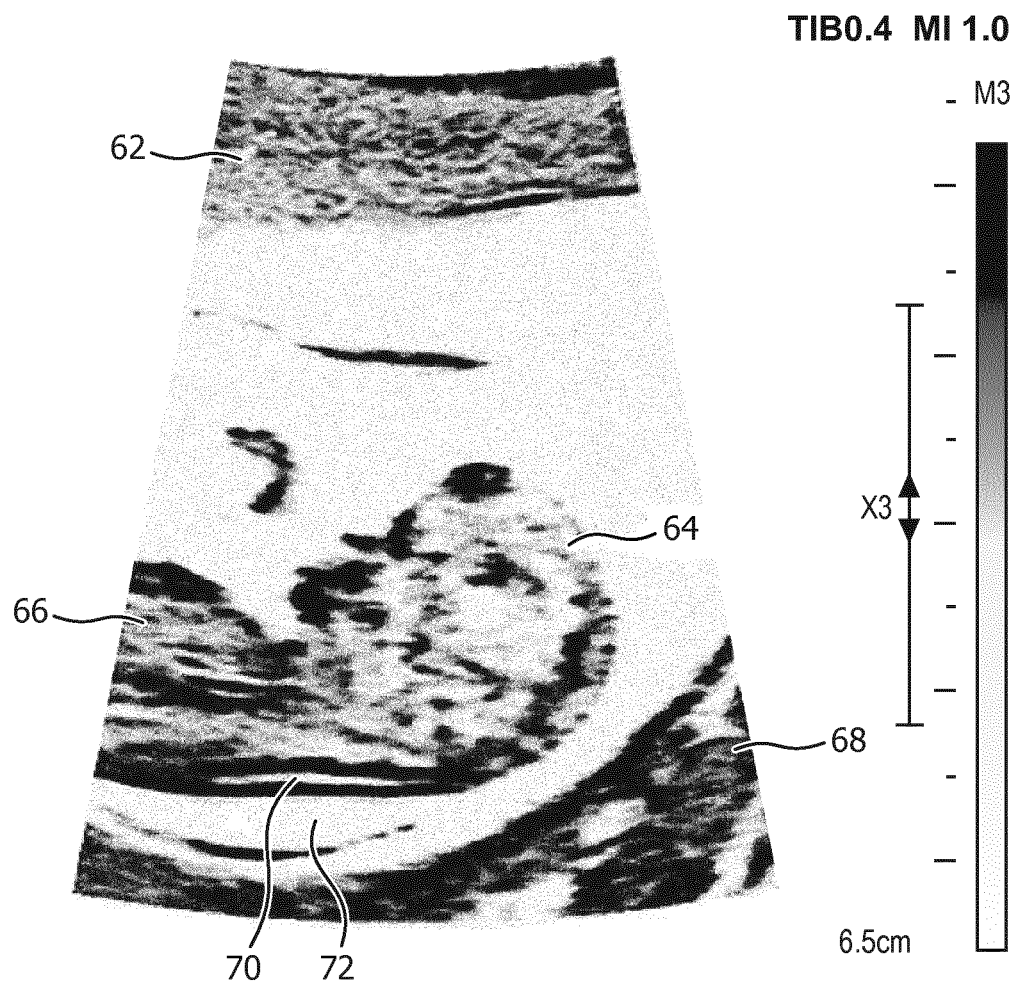
FIG. 1 is a screenshot of an ultrasound image of a fetus in the proper position for a nuchal translucency measurement.

Referring first to FIG. 1, a screenshot of an ultrasound image 62 of a fetus in the proper position for a nuchal translucency measurement is shown. This ultrasound image was made using a curved linear array transducer probe with the image plane positioned to capture the fetus in a sagittal cross-sectional view. This view intersects the nuchal translucent region 70 at the nape of the fetal neck. The fetal head 64 and thorax 66 are relaxed and not flexed, which would tend to compress the translucent region and distort the measurement. The fetus is also floating freely away from the uterine wall 68 with a region 72 of amniotic fluid between the fetus and the wall of the uterus.

Figure 2:
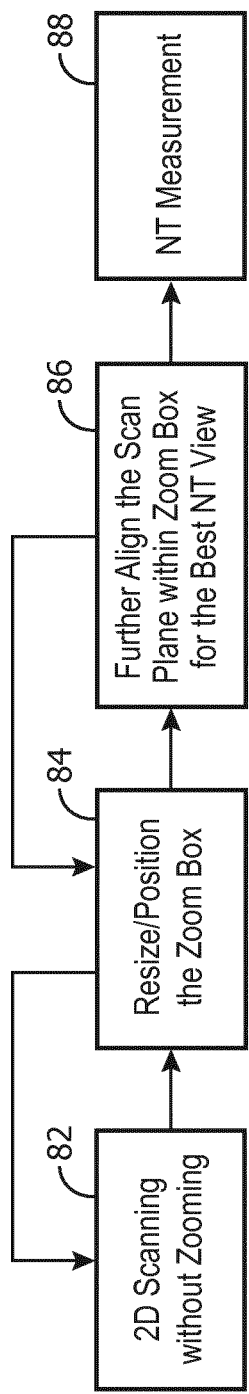
FIG. 2 is a flowchart of the standard diagnostic workflow for a nuchal translucency measurement.

The standard clinical procedure for making a nuchal translucency (NT) measurement is shown in the flowchart of FIG. 2. There are four major steps in the NT workflow. A normal two dimensional ultrasonic image scan of the fetus is done first, as indicated in step 82. A control of the ultrasound system is manipulated to call up a graphic overlay of a zoom box over the image. The region of the image contained within the zoom box will be enlarged (zoomed) to magnify the NT region where the measurement is made, easing the positioning of calipers over and in alignment with the small NT gap where the measurement is to be made. The sonographer usually needs to readjust the size and position of the zoom box a number of times to have the zoom box filled with the fetal head and thorax and appropriately enlarged for the measurement, as shown in step 84. In addition, the sonographer will often have to wait for a moving fetus to assume the desired position inside the zoom box, in the sagittal orientation with the back of the neck facing downward and no flexure of the neck or thorax, as indicated by step 86. In the cases when the above criteria are not satisfied due to the motion from the fetus, the mother, or the probe, the sonographer may need to go back to step 84 or step 82 from step 86, and repeat those steps to obtain the correct image capture, as indicated by the return arrows in FIG. 2. Once the proper view is found, the sonographer will freeze the image and make the NT measurement in step 88.

Figure 3:
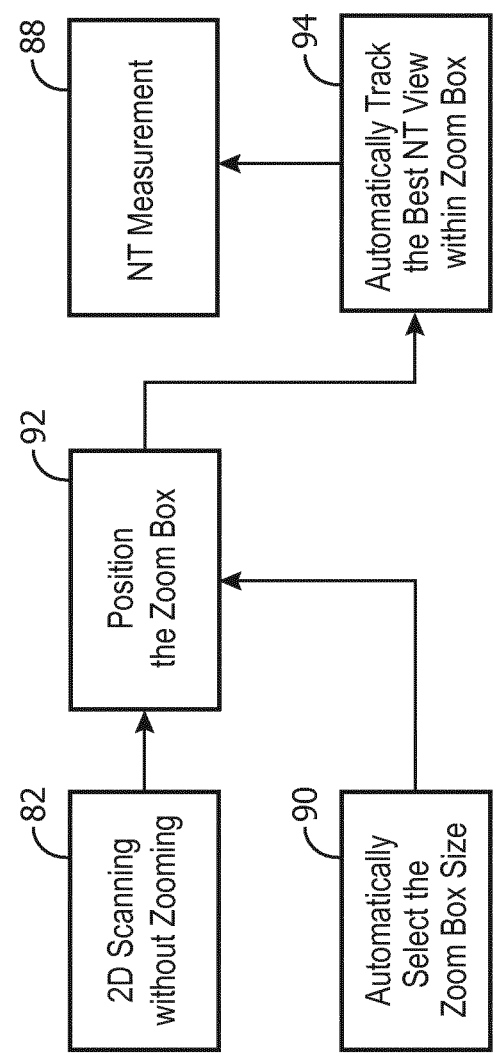
FIG. 3 is a flowchart of a workflow for a nuchal translucency measurement in accordance with the principles of the present invention.

Depending on the behavior of the fetus, the patient and the technique and experience of the sonographer, the iterations in the workflow of FIG. 2 can be very time consuming. In order to address this problem, an implementation of the present invention includes automatic zoom box sizing and fetal position tracking to assist and expedite the NT measurement. A software program in the ultrasound system or diagnostic workstation will automatically calculate the magnification factor and zoom box size based on the gestational age of the fetus as shown in step 90 of FIG. 3. In this way, the sonographer only needs to choose the zoom box position as shown in step 92 without the need to select the zoom box size. Once the sonographer or diagnostician chooses the position of the zoom box and commands the system to enter the zoom-in mode, the software program automatically tracks the fetus translation motion as long as it is within the image plane. An automatic algorithm executed by the software helps the user obtain a good image for accurate NT measurement faster and easier, reducing workflow redundancy and reducing scanning time in NT scans compared with the standard practice.

Figure 4:
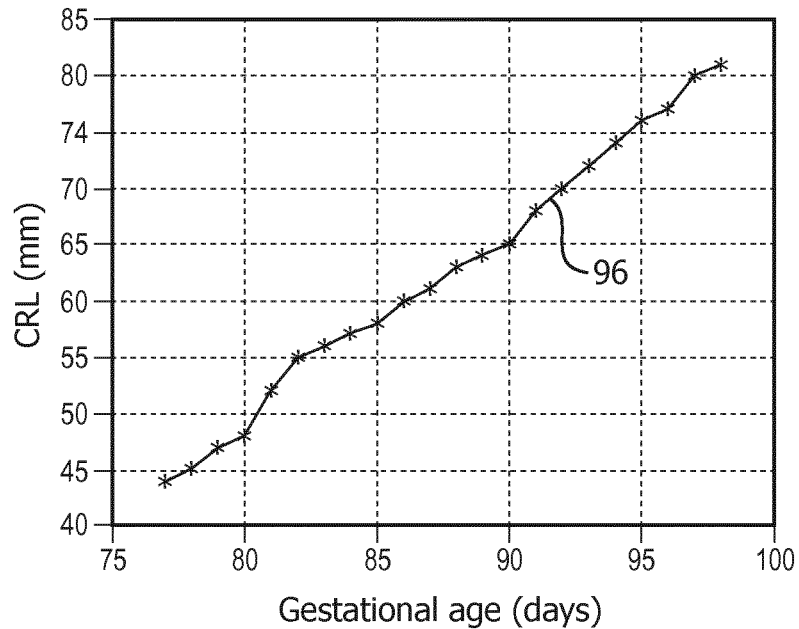
FIG. 4 is a graph of fetal crown-rump length development with gestational age.

FIG. 4 is a graph of nominal crown-rump length of a fetus as it relates to gestational age. As the line 96 of the graph shows, this is approximately a linear relationship. Once the gestational age is known, which may be input into the ultrasound system as part of the patient data entered at the outset of the exam or calculated from measurements made of fetal anatomy, the ultrasound system sets the size of the zoom box in accordance with this linear relationship. The size of the zoom box may be set to have a length and width which are 80%-100% of the crown-rump length, for example, with a magnification factor that fills the box with the upper thorax and head region of the fetus. An appropriately sized zoom box is automatically set by the system, sparing the user from an otherwise manual and often repetitive step of the standard workflow.

When a sonographer performs an NT exam, the sonographer manipulates the ultrasound probe to acquire a sagittal image of the region of interest of the fetus, the head and upper thorax. When a 2D probe is used, the sonographer manipulates the single image plane of the probe to intersect the fetus in this desired view. When a 3D probe is used, the sonographer can acquire a volume of image data encompassing the region of the fetus, then select an MPR (multi-planar reformatted) image plane through the data which contains the desired sagittal view. This is done in live imaging mode. When the sonographer sees the region of interest in the image, the user calls up a zoom box with appropriate size to include this imaging area. The zoom box is generally manipulated by dragging it into the proper position over the image. After this step and before the sonographer can capture an image for NT measurement, the fetus is likely to move around to a different position in the uterus. In accordance with a further aspect of the present invention the NT diagnostic software includes a tracking algorithm to follow the region of interest as the fetus moves, thereby assisting the sonographer in scanning or waiting for the fetus to return to a position where the proper view can be acquired, a view of the mid-nasal sagittal image plane. With the region of interest inside of the zoom box, the sonographer points to the region of interest with a graphic pointer such as by clicking on the region of interest with a mouse or trackball or touching the region of interest on a touch screen. The tracking algorithm then automatically tracks this area temporally from frame to frame as the fetus moves. The sonographer can then wait for the fetus to move into a favorable position for the NT measurement. A preferred tracking algorithm only computes position updates of translation motion from frame to frame; rotational motion tracking is not required. FIG. 7 illustrates examples of this feature tracking. Suppose the user acquires a sagittal image of the fetus in a favorable position for the NT measurement, and zooms in on the head and neck of the fetus in the zoom box 100 as shown in FIG. 7a. With the sonographer about to make the MT measurement, the fetus moves to a different position in the uterus as shown in FIG. 7b. In this new position, most of the nuchal translucent region 70 is outside of the zoom box 100. Without automatic tracking, the sonographer would have to make the adjustments listed in steps 82, 84, and 86 of FIG. 2, acquiring a new fetal image, resizing and/or repositioning the zoom box 100, and/or realigning the scan plane within the zoom box. But with an automatic tracking algorithm, the zoom box 100 will follow the NT region in real time as shown in FIG. 7c. It is seen from a comparison of the fetal position in FIGS. 7a and 7c that the fetus has rotated in position from one image to another. While this rotation causes the nuchal translucent region 70 to rotate within the zoom box, this does not prevent an accurate NT measurement as the region 70 is still entirely within the zoom box due to translational tracking. It is thus not necessary to employ rotational tracking or adjustment in the tracking algorithm. The sonographer can then wait for the fetus to rotate back to a more favorable view, if desired, such as that shown in FIG. 7a, before making the NT measurement.

Figure 5:
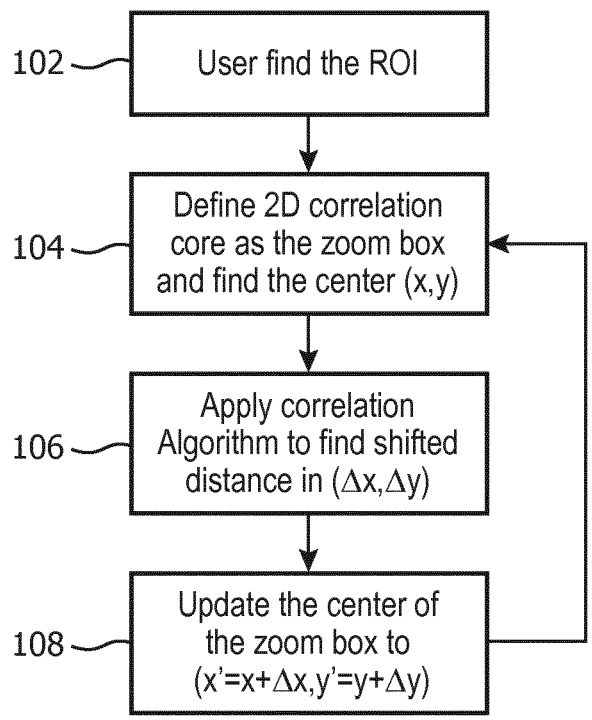
FIG. 5 is a flowchart of an algorithm for fetal tracking in accordance with the principles of the present invention.

A flowchart of a suitable tracking algorithm for an implementation of the present invention is shown in FIG. 5. In step 102 the sonographer finds the region of interest in the fetal image, such as the head-thorax region or the nape of the fetal neck. With the zoom box 100 positioned over the image to encompass the region of interest, a 2D correlation core for tracking is defined as the region within the zoom box in step 104. Preferably the correlation core should include some easily tracked image characteristics such as the head bone structure. The coordinate at the center of the correlation core (x,y) is then found. This can be done manually by the sonographer clicking at the center of the zoom box, or the diagnostic software can find the center of the zoom box simply from the coordinates of the zoom box in relation to the fetus. In step 106 a correlation algorithm, which is described further below, is executed on the image (pixel) data of each temporally new image to find any motion-shifted distance of the correlation core coordinates ($\Delta x, \Delta y$). The center of the zoom box is updated to the new location of the image structure in step 108 using the equations $x'=x+\Delta x$ and $y'=y+\Delta y$. The most recent image frame is set to be the reference frame for the next iteration of the tracking algorithm and the process loops back to step 104. The position of the zoom box on the display is updated to the new zoom box center, thus repositioning the zoom box in an effort to keep the region of interest within the zoom box as the fetus moves.

Figure 6:
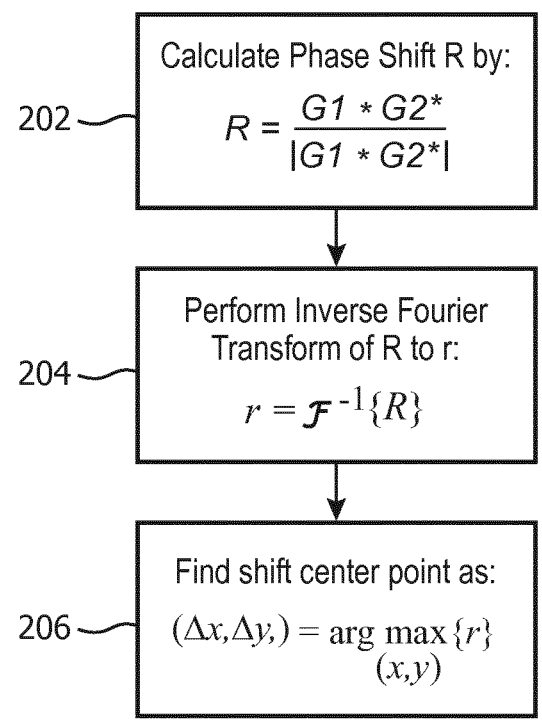
FIG. 6 is a flowchart of a correlation algorithm for tracking the center of a zoom box in accordance with the present invention.

FIG. 6 is a flowchart illustrating a suitable correlation algorithm for use in an implementation of the present invention. This algorithm employs a 2D transform of the coordinates of the reference image data (A1) and the new image data (A2) to Fourier data sets G1 and G2, respectively. In step 202 the phase shift R in Fourier space caused by the frame-to-frame motion is calculated by:

$$R = \frac{G1 * G2^*}{|G1 * G2^*|}$$

In step 204 an inverse Fourier transform of R to r in Cartesian coordinates is performed by:

$$r = \mathcal{F}^{-1}\{R\}$$

The shifted distance of the center of the correlation core is found by:

$$(\Delta x, \Delta y) = \arg \max_{(x,y)} \{r\}$$

The process then goes to step 108 of the tracking algorithm as discussed above.

Referring to FIG. 8, an ultrasound system constructed in accordance with the principles of the present invention is shown in block diagram form. An ultrasonic probe 12 includes an array 14 of ultrasonic transducer elements that transmit and receive ultrasonic pulses. The array may be a one dimensional linear or curved array for two dimensional imaging, or may be a two dimensional matrix of transducer elements for electronic beam steering in three dimensions. The array may also be a one dimensional array that is mechanically swept back and forth by the probe to scan a three dimensional volume of the body. The ultrasonic transducers in the array 14 transmit ultrasonic energy and receive echoes returned in response to this transmission. A transmit/receive ("T/R") switch 22 is coupled to the ultrasonic transducers in the array 14 to selectively couple signals received from the transducer elements to A/D converters 30 during the receive phase of operation. The times at which the transducer array is activated to transmit signals may be synchronized to an internal system clock (not shown), or may be synchronized to a bodily function such as the patient heart cycle, for which a heart cycle waveform is provided by an ECG device 26. In obstetrical imaging of a fetus, heart cycle synchronization is generally not employed.

Echoes from the transmitted ultrasonic energy are received by the transducer elements of the array 14, which generate echo signals that are coupled through the T/R switch 22 and digitized by analog to digital ("A/D") converters 30 when the system uses a digital beamformer. Analog beamformers may alternatively be used. The A/D converters 30 sample the received echo signals at a sampling frequency controlled by a signal f generated by a central controller 28. The desired sampling rate dictated by sampling theory is at least twice the highest frequency of the received passband, and might be on the order of 30-40 MHz. Sampling rates higher than the minimum requirement are also desirable. Control of the ultrasound system and the setting of various parameters for imaging such as probe selection, zoom box control, and NT measurement caliper adjustment is effected by user manipulation of the controls of a control panel 20 which is coupled to and applies its control through the central controller 28.

The echo signal samples from the individual transducers of the array 14 are delayed and summed by a beamformer 32 to form coherent echo signals. For 3D imaging with a two dimensional array, it is preferable to partition the beamforming process between a microbeamformer located in the probe and the main beamformer in the system mainframe as described in U.S. Pat. No. 6,013,032 (Savord) and U.S. Pat. No. 6,375,617 (Fraser). The digital coherent echo signals are then filtered by a digital filter 34. The digital filter 34 bandpass filters the signals, and can also shift the frequency band to a lower or baseband frequency range. The digital filter could be a filter of the type disclosed in U.S. Pat. No. 6,050,942 (Rust et al.), for example. Filtered echo signals from tissue are coupled from the digital filter 34 to a B mode processor 36 for conventional B mode processing by echo signal amplitude detection.

Filtered echo signals of a contrast agent, such as microbubbles, are coupled to a contrast signal processor 38. Contrast agents are often used to more clearly delineate blood vessels, or to perform perfusion studies of the microvasculature of tissue as described in U.S. Pat. No. 6,692,438 (Skyba et al.) for example. The contrast signal processor 38 preferably separates echoes returned from harmonic contrast agents by the pulse inversion technique, in which echoes resulting from the transmission of multiple pulses to an image location are combined to cancel fundamental signal components and enhance harmonic components. A preferred pulse inversion technique is described in U.S. Pat. No. 6,186,950 (Averkiou et al.), for instance.

The filtered echo signals from the digital filter 34 are also coupled to a Doppler processor 40 for conventional Doppler processing to produce velocity and/or power Doppler signals from blood flow or tissue motion. The output signals from these processors may be converted into a desired image format by a scan converter and displayed as planar images, and are also coupled to a 3D image processor 42 for the rendering of three dimensional images, which are stored in a 3D image memory 44. Three dimensional rendering may be performed as described in U.S. Pat. No. 5,720,291 (Schwartz), and in U.S. Pat. No. 5,474,073 (Schwartz et al.) and U.S. Pat. No. 5,485,842 (Quistgaard), all of which are incorporated herein by reference.

The two dimensional image signals from these three image processors, the contrast signal processor 38, the B mode processor 36 and the Doppler processor 40, and the three dimensional image signals from the 3D image memory 44, are coupled to a Cineloop® memory 48, which stores temporally successive image data for each of a large number of ultrasonic images. The image data are preferably stored in the Cineloop memory 48 in sets, with each set of image data corresponding to an image obtained at a respective time. The image data in a group can be used to display a parametric image showing tissue perfusion at a respective time during the heartbeat. The groups of image data stored in the Cineloop memory 48 may also be stored in a permanent memory device such as a disk drive, solid state memory device, or digital video recorder for later analysis. In this embodiment the images are also coupled to a QLAB processor 50, where the images are analyzed and measurements made of characteristics of the images including the nuchal translucency workflow and measurements described above. The QLAB processor is a software package stored on the ultrasound system disk drive or solid state memory that is commercially available with Philips Healthcare ultrasound systems for various image analysis and quantification procedures. The QLAB processor can be used to make quantified measurements of various aspects of the anatomy in the image such as the delineation of tissue boundaries and borders by automated border tracing as described in US patent publication no. 2005-0075567 and PCT publication no. 2005/054898. The QLAB processor is controlled through user manipulation of controls such as a keyboard, mouse, buttons and trackball of the control panel 20. The data and images produced by the QLAB processor are displayed on a display 52 such as a flat panel display monitor where the user may manipulate, annotate and make measurements of the displayed images through operation of the controls of the control panel 20 as described above for a nuchal translucency exam. The QLAB processor thus implements a fully capable nuchal translucency measurement processor which can implements the NT workflows of the present invention, such as the workflow shown in FIG. 3. At the conclusion of an ultrasound exam, the images acquired and diagnostic reports made on the ultrasound system can be stored on a PACS (picture archiving and communication system) 60 for storage and later retrieval.

The ultrasound system components and processors of FIG. 8 may be implemented utilizing any combination of dedicated hardware boards, DSPs, microprocessors, etc. and software programs stored on a system disk drive or solid state memory. Alternatively, the functionality and components of the system may be implemented utilizing an off-the-shelf PC with a single microprocessor or multiple microprocessors, with the functional operations distributed between the processors. As a further option, the functionality of FIG. 8 may be implemented utilizing a hybrid configuration in which certain modular functions are performed utilizing dedicated hardware, while the remaining modular functions are performed utilizing an off-the shelf PC, software and the like. An example of this configuration is a probe containing the transducer array and microbeamformer to produce beamformed echo signals, which are then further processed to produce images entirely by software programs of a tablet computer, on which the final images are displayed. The Philips Healthcare Visiq ultrasound system is an example of such a system implementation, in which all of the ultrasound system functionality after beamforming is performed by software executed by the tablet microprocessor. The various functions of the blocks shown in FIG. 8 also may be implemented as software modules within a processing unit. The ultrasound system of FIG. 8 may be embodied as a small-sized system, such as laptop computer or pocket sized system as well as in a larger console-type or cart-borne system. These different embodiments may be implemented in connection with miniaturized or small-sized ultrasound systems having different dimensions, weights, and power consumption. For example, the a pocket-sized ultrasound imaging system implementation and a miniaturized laptop-like or tablet style ultrasound system implementation can provide the same scanning and processing functionality as a large hardware-intensive cart-borne system, primarily due to the ability to perform much of the system functionality by the execution of software programs.

It should be noted that the various embodiments described above and illustrated by the exemplary ultrasound system of FIG. 8 may be implemented in hardware, software or a combination thereof. The various embodiments and/or components, for example, the modules, or components and controllers therein, also may be implemented as part of one or more computers or microprocessors. The computer or processor may include a computing device, an input device, a display unit and an interface, for example, for accessing the Internet. The computer or processor may include a microprocessor. The microprocessor may be connected to a communication bus, for example, to access a PACS system. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, non-volatile RAM (NVRAM) memory and electromagnetic or optical disk storage. The above memory types are exemplary only, and are thus not limiting as to the types of memory usable for storage of a computer program.

It is to be understood that the above description is intended to be illustrative, and not restrictive. For example, many modifications may be made to adapt a particular situation or material to the teachings of the various embodiments without departing from their scope. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasonic diagnostic imaging system for performing a nuchal translucency measurement, the system comprising instructions thereon, which when executed, cause the system to:
    acquire, using an ultrasound probe, ultrasound image data;
    produce fetal ultrasound images from the ultrasound image data, the fetal ultrasound images comprising at least a portion of a fetus;
    display successive fetal ultrasound image frames;
    position a zoom box over a nuchal fold of the fetus, wherein the zoom box delineates an image which has been enlarged based on a magnification factor and wherein a size of the zoom box is automatically set by the system based on a gestational age of the fetus;
    track fetal image data within the zoom box from frame to frame in the successive frames; and
    analyze the nuchal fold in one or more of the fetal ultrasound images to perform a nuchal translucency measurement.

2. The ultrasonic diagnostic imaging system of claim 1, wherein the size of the zoom box is further based on a crown rump length of the fetus.

3. The ultrasonic diagnostic imaging system of claim 1, wherein gestational age is based on patient data manually input into the ultrasound system.

4. The ultrasonic diagnostic imaging system of claim 1, wherein gestational age is based on fetal anatomy characteristics.

5. The ultrasonic diagnostic imaging system of claim 1, wherein the instructions further cause the system to track fetal motion in a uterus.

6. The ultrasonic diagnostic imaging system of claim 1, wherein the instructions further cause the system to track changes in a position of the fetus from frame to frame.

7. The ultrasonic diagnostic imaging system of claim 6, wherein the instructions further cause the system to reposition the zoom box over the fetal image in response to a change in fetal position.

8. The ultrasonic diagnostic imaging system of claim 1, wherein the instructions further cause the system to automatically calculate the magnification factor for the image within the zoom box.

9. The ultrasonic diagnostic imaging system of claim 8, wherein the magnification factor is calculated based on the gestational age of the fetus.

10. The ultrasonic diagnostic imaging system of claim 8, wherein the size of the zoom box and the magnification factor are set such that the zoom box shows only an upper thorax and head region of the fetus.

11. The ultrasonic diagnostic imaging system of claim 2, wherein the size of the zoom box is set to between 80% and 100% the size of the crown rump length of the fetus.

12. The ultrasonic diagnostic imaging system of claim 7, wherein the instructions further cause the system to calculate a change in fetal position from one image frame to another by 2D correlation of image data from frame to frame.

13. A method of performing a nuchal translucency exam comprising:
    acquiring an ultrasound image of a fetus including a nuchal translucency region of interest;
    positioning a zoom box over the nuchal translucency region of interest, wherein the zoom box delineates an image which has been enlarged based on a magnification factor, and the zoom box size is automatically set for a user based on a gestational age of the fetus;
    automatically tracking fetal motion within the zoom box in real time; and
    making a nuchal translucency measurement.

14. The method of claim 13, wherein the zoom box size is based on a crown rump length of the fetus.

15. The method of claim 13, wherein automatically tracking fetal motion further comprises determining a change in fetal position between temporally different image frames.

16. The method of claim 15, wherein automatically tracking fetal motion further comprises repositioning the zoom box over the fetal image in response to a change in fetal position.

17. The method of claim 16, wherein automatically tracking fetal motion further comprises calculating a change in fetal position from one temporal image frame to another by 2D correlation of image data from frame to frame.

* * * * *